United States Patent
Liu et al.

(10) Patent No.: US 10,774,110 B2
(45) Date of Patent: Sep. 15, 2020

(54) RAPADOCINS, INHIBITORS OF EQUILIBRATIVE NUCLEOSIDE TRANSPORTER 1 AND USES THEREOF

(71) Applicant: The Johns Hopkins University, Baltimore, MD (US)

(72) Inventors: Jun Liu, Baltimore, MD (US); Jingxin Wang, Baltimore, MD (US); Zhaoli Sun, Baltimore, MD (US); Sam Hong, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 45 days.

(21) Appl. No.: 16/073,746

(22) PCT Filed: Feb. 3, 2017

(86) PCT No.: PCT/US2017/016494
§ 371 (c)(1),
(2) Date: Jul. 27, 2018

(87) PCT Pub. No.: WO2017/136717
PCT Pub. Date: Aug. 10, 2017

(65) Prior Publication Data
US 2019/0031716 A1 Jan. 31, 2019

Related U.S. Application Data

(60) Provisional application No. 62/291,428, filed on Feb. 4, 2016.

(51) Int. Cl.
| | |
|---|---|
| *A61K 38/00* | (2006.01) |
| *A61P 5/00* | (2006.01) |
| *C07K 5/103* | (2006.01) |
| *C07D 498/18* | (2006.01) |
| *C07D 519/00* | (2006.01) |
| *A61K 47/54* | (2017.01) |
| *A61K 38/07* | (2006.01) |

(52) U.S. Cl.
CPC ............ *C07K 5/1008* (2013.01); *A61K 38/07* (2013.01); *A61K 47/545* (2017.08); *C07D 498/18* (2013.01); *C07D 519/00* (2013.01)

(58) Field of Classification Search
None
See application file for complete search history.

(56) References Cited

U.S. PATENT DOCUMENTS

| 5,457,194 A | 10/1995 | Luly |
| 8,956,825 B2 | 2/2015 | Weisbart |
| 9,250,237 B2 | 2/2016 | Liu et al. |

| 2006/0003362 A1 | 1/2006 | Zerangue |
| 2008/0292618 A1 | 11/2008 | Weisbart |
| 2014/0073581 A1 | 3/2014 | Liu et al. |

FOREIGN PATENT DOCUMENTS

| WO | WO 2017/136708 A1 | 8/2017 |
| WO | WO 2017/136731 A1 | 8/2017 |

OTHER PUBLICATIONS

Choi et al. "Structure of the FKBP12-Rapamycin Complex Interacting with the Binding Domain of Human FRAP" Science 273:239-242. (Year: 1996).*
Nakanishi, Takeo, "Drug Transporters as Targets for Cancer Chemotherapy," *Cancer Genomics & Proteomics* (2007), 4:241-254.
Extended European Search Report dated Jul. 16, 2019, regarding EP 17 74 8270.
Guo, Zufeng et al.: "*Rapamycin-inspired macrocycles with new target specificity*"; Nature Chemistry, vol. 11, No. 3, Dec. 10, 2018, pp. 254-263, XP036706998, ISSN: 1755-4330, DOI: 10.1038/S41557-018-0187-4. [retrieved on Dec. 10, 2018].
Huang, M. et al.: "*Inhibition of Nucleoside Transport by Protein Kinase Inhibitors*"; J. Pharmacology and Experimental Therapeutics, vol. 304, No. 2, Jan. 1, 2003, pp. 753-760, XP008036291, ISSN: 0022-3565, DOI: 10.1124/JPET.102.044214.

* cited by examiner

*Primary Examiner* — James H Alstrum-Acevedo
*Assistant Examiner* — Zachary J Miknis
(74) *Attorney, Agent, or Firm* — DLA Piper LLP (US)

(57) ABSTRACT

A compound of Formula (I), and its analogs are provided. Compositions that include Formula I can be used to inhibit human equilibrative nucleoside transporter 1, increase adenosine signaling and produce effects that include increasing antiviral activity, increasing antiparasitic activity, increasing alcohol tolerance, decreasing pain protecting from ischemia as well as many other conditions.

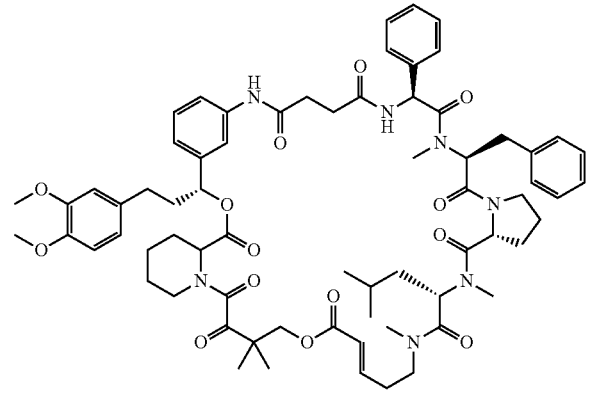

(I)

4 Claims, 4 Drawing Sheets

RAPADOCINS, INHIBITORS OF EQUILIBRATIVE NUCLEOSIDE TRANSPORTER 1 AND USES THEREOF

CROSS-REFERENCE TO RELATED APPLICATIONS

This application is a 35 USC § 371 National Stage application of International Application No. PCT/US2017/016494 filed Feb. 3, 2017, now pending; which claims the benefit under 35 USC § 119(e) to U.S. Application Ser. No. 62/291,428 filed Feb. 4, 2016. The disclosure of each of the prior applications is considered part of and is incorporated by reference in the disclosure of this application.

GRANT INFORMATION

This invention was made with government support under CA174428, awarded by the National Institutes of Health. The government has certain rights in the invention.

BACKGROUND OF THE INVENTION

Field of the Invention

The present invention relates generally to small molecule compounds and more specifically to the use of such compounds for inhibiting human equilibrative nucleoside transporter 1 (ENT1).

Background Information

Transporter proteins are involved in the cellular uptake of various molecules into and/or through cells. Carrier-mediated transport systems use proteins that are anchored to the cell membrane, typically by a plurality of membrane-spanning domains and function by transporting their substrates via active or passive mechanisms. Carrier-mediated transport systems are involved in the active or non-active, facilitated transport of many important nutrients such as vitamins, sugars, and amino acids. Carrier-mediated transporters are also present in organs such as the liver and kidney, in which the proteins are involved in the excretion or re-absorption of circulating compounds. Polar or hydrophilic compounds typically diffuse poorly across the lipid bilayers that constitute cellular membranes. For many small molecules (e.g., amino acids, di- and tripeptides, monosaccharides, nucleosides and water-soluble vitamins) there exist specific carrier-mediated transporters for active transport of the solute molecules across biological membranes.

The uptake or release of physiological nucleosides and many of their synthetic analogs by mammalian cells occurs primarily by means of specific carrier-mediated transporters known as nucleoside transporters. Nucleoside transporters have been classified into two categories: (i) equilibrative (facilitated diffusion) and (ii) concentrative (secondary active) sodium-dependent. Two equilibrative transport systems with similar broad substrate specificities have been identified and designated as the es (equilibrative sensitive) and ei (equilibrative insensitive) transporters, on the basis of their sensitivity or insensitivity to inhibition by nitrobenzyl-thioinosine (NBMPR, 1), respectively.

Specific transporters are required for the permeation of nucleosides across cell membranes. Among the family of nucleoside transporters the equilibrative nucleoside transporters (ENTs) are the most broadly expressed and four human ENTs have been identified in humans: hENT-1, hENT-2, hENT-3 and hENT-4. The most thoroughly characterized are hENT-1 and hENT-2 which are cell surface proteins and are broadly selective for both purine and pyrimidine nucleosides. They can be distinguished from each other by their sensitivities to inhibition by nitrobenzylmercaptopurine riboside (NBMPR). ENT1 is potently inhibited by nanomolar concentrations of NBMPR and is therefore also called a NBMPR sensitive equilibrative nucleoside transport protein. ENT2 is insensitive to nanomolar concentrations of NBMPR, but can be inhibited by higher (micromolar) concentrations of NBMPR and is therefore also referred to as a NBMPR insensitive equilibrative nucleoside transport protein (iENTP) (see Griffith et al Biochim. Bioph. Acta 1286:153-181 (1986)).

Human equilibrative nucleoside transporter 1 (ENT1) is encoded by the SLC29a1 gene. The gene is a member of the equilibrative nucleoside transporter family. The gene encodes a transmembrane glycoprotein that localizes to the plasma and mitochondrial membranes and mediates the cellular uptake of nucleosides from the surrounding medium. The protein is categorized as an equilibrative (as opposed to concentrative) transporter that is sensitive to inhibition by nitrobenzylmercaptopurine ribonucleoside (NBMPR). Nucleoside transporters are required for nucleotide synthesis in cells that lack de novo nucleoside synthesis pathways, and are also necessary for the uptake of cytotoxic nucleosides used for cancer and viral chemotherapies.

Adenosine is an endogenous purine nucleoside that is particularly released in pathophysiological conditions like ischemia, inflammation and pain. Under these circumstances it plays an important neuro- and immunomodulatory role. Adenosine administration is analgesic in various nociceptive modalities in humans. Because of the short half-life of adenosine and side-effects caused by its administration, there has been considerable interest in finding ways to reinforce the effects of endogenous adenosine. Inhibition of the ENT1 blocks uptake of adenosine into cells and could enhance its beneficial effects.

SUMMARY OF THE INVENTION

In one embodiment, the invention provides compounds that include the following: Formula I, Formula II, Formula III, Formula IV, Formula V, Formula VI, Formula VII, Formula VIII, Formula IX, Formula X, Formula XI, XII JW95-1, JW95-2, JW95-3, JW95-4, JW95-5, JW95-6, JW95-7, JW95-8, JW95-9, JW95-10, JW95-11, JW95-12, JW95-13, JW95-14, JW95-15, JW95-16, JW95-17, JW95-18, JW95-19, JW95-20, JW95-21, JW95-22, JW95-23, JW95-24, JW95-25, 95-15-1, 95-15-2, 95-15-3, 95-15-4, 95-15-5, 95-15-6, 95-15-7, 95-15-8, 95-15-9, 95-15-10, 95-15-11, 95-15-12, 95-15-13, 95-15-14, 95-15-15, 95-15-16, 95-15-17, 95-15-18, 95-15-19, 95-15-20, 95-15-21, 95-15-22, 95-15-23, 95-15-13-2, 95-15-13-3, 95-15-13-4, 95-15-13-5, 95-15-13-6, 95-15-13-7, 95-15-13-8, 95-15-13-9, 95-15-13-10, 95-15-13-11, 95-15-13-12, 95-15-13-13, 95-15-13-14, 95-15-13-15 and JW95S2Biotin. The compounds are illustrated in the structures provided herein.

Another embodiment of the present invention is to provide a method of inhibiting human equilibrative nucleoside transporter 1 (ENT1) that includes administering to a subject in need thereof an effective amount of compound listed above.

Another embodiment of the present invention is to provide a method of increasing adenosine signaling that includes administering to a subject in need thereof an effective amount of a compound listed above.

Another embodiment of the present invention is to provide a method of increasing adenosine signaling that includes administering to a subject in need thereof an effective amount of a compound listed above. The administering of the aforementioned compound results in one or more of the following effects: increase in antiviral activity, increase in antiparasitic activity, increase in alcohol tolerance, decrease in pain and protection from ischemia, attenuation of epileptic seizure severity, lessening of erectile dysfunction, improvement of liver function, improvement of respiratory disorders, improvement of sepsis, improvement of thrombosis, improvement of hypertension, improvement of inflammatory disorders, improvement of allergies, improvement of cardiac ischemias, improvement of arrhythmias, improvement of Parkinson's disease, improvement of chronic heart failure, improvement of rheumatoid arthritis, improvement of dry eye disease, improvement of chronic plaque type psoriasis, improvement of chronic neuropathological pain and improvement of sickle cell disease.

Another embodiment of the present invention is to provide a compound with the following structure:

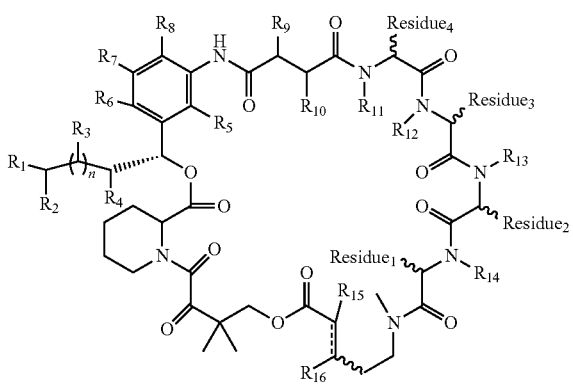

n = 0-6

$R_1$:

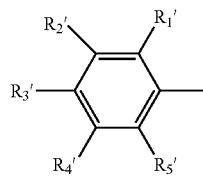

Wherein $R_1'-R_3'$=OH, $NH_2$, CN, OAc. or OMe individually or in combination.

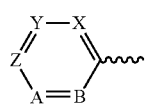

Wherein: A, B, X, Y, Z=C, N, or P either individually or in combination.

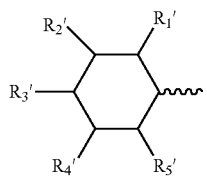

Wherein $R_1'-R_5'$=OH, $NH_2$, SH, H, OAc, OMe individually or in combination.

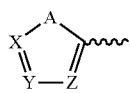

Wherein A, X, Y, or Z=CHn' (n'=0-2), O, N, S, wherever appropriate. Individually or in combination.

$R_2-R_4$=H, methyl, ethyl, propyl, isopropyl, phenyl, OH, $NH_2$. SH, CN, individually or in combination.

$R_5-R_8$ methyl, ethyl, propyl, isopropyl, phenyl, OH, $NH_2$, SH, CN, individually or in combination.

$R_9$=OH, $NH_2$, SH, CN, H;

$R_{10}$=OH, $NH_2$, SH, CN, H.

$R_{11-14}$=H or Me.

$R_{15}$=OH, $NH_2$, SH, CN, H;

$R_{16}$=OH, $NH_2$, SH, CN, H.

The bond between the carbons bearing $R_{15}$ and $R_{16}$ can be either a single or a double bond in either E or Z configuration.

wherein residues 1-4 can be any amino acid building block listed in below or its modified version

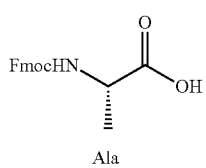

Ala

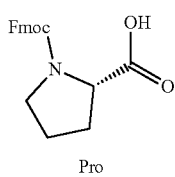

Pro

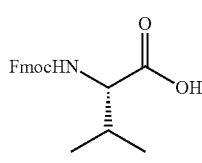

Val

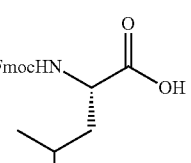

Leu

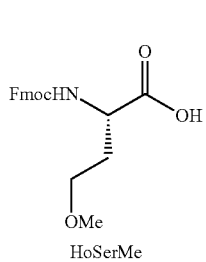

HoSerMe

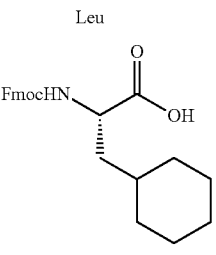

ChA

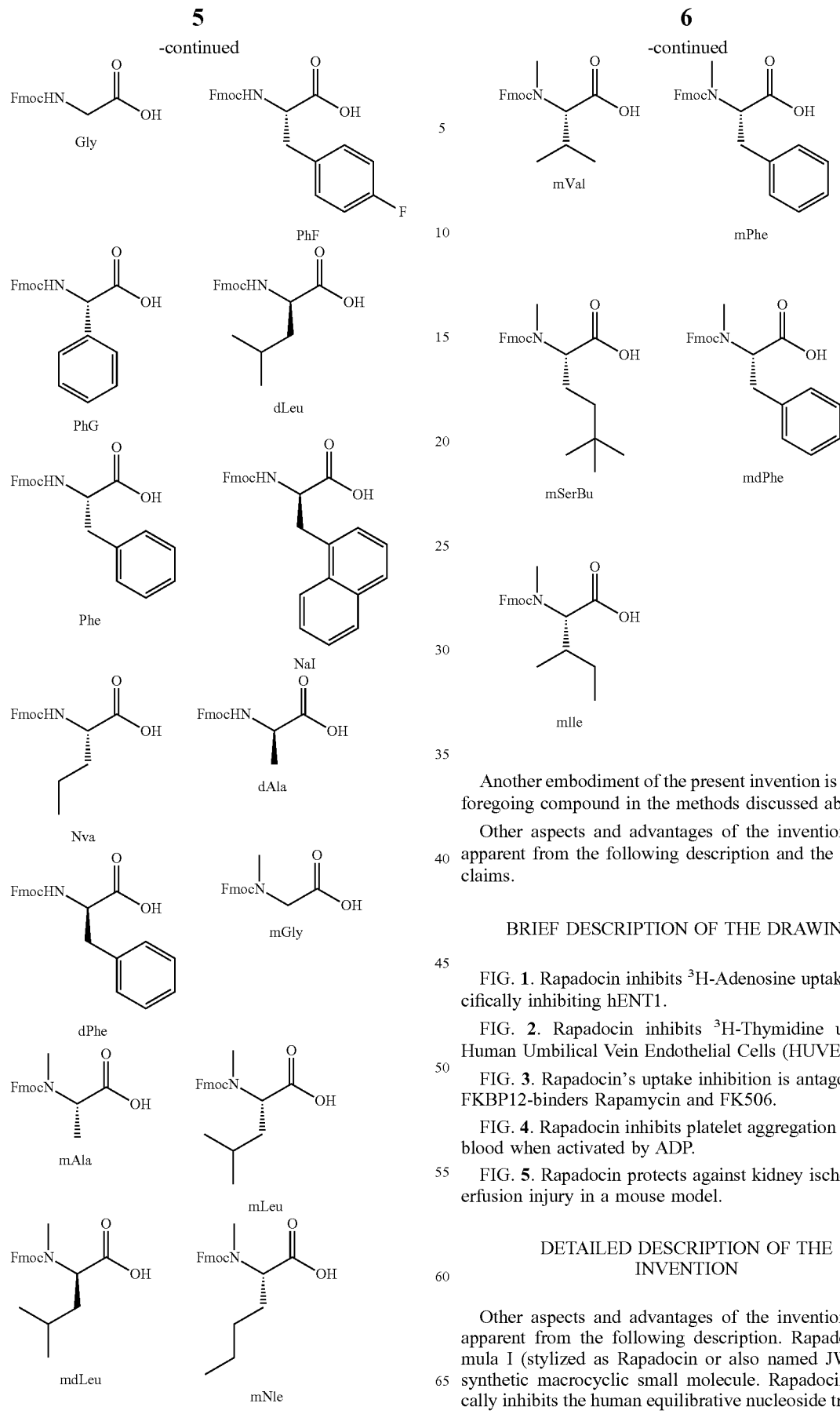

Another embodiment of the present invention is to use the foregoing compound in the methods discussed above.

Other aspects and advantages of the invention will be apparent from the following description and the appended claims.

DETAILED DESCRIPTION OF THE INVENTION

Figure 1:
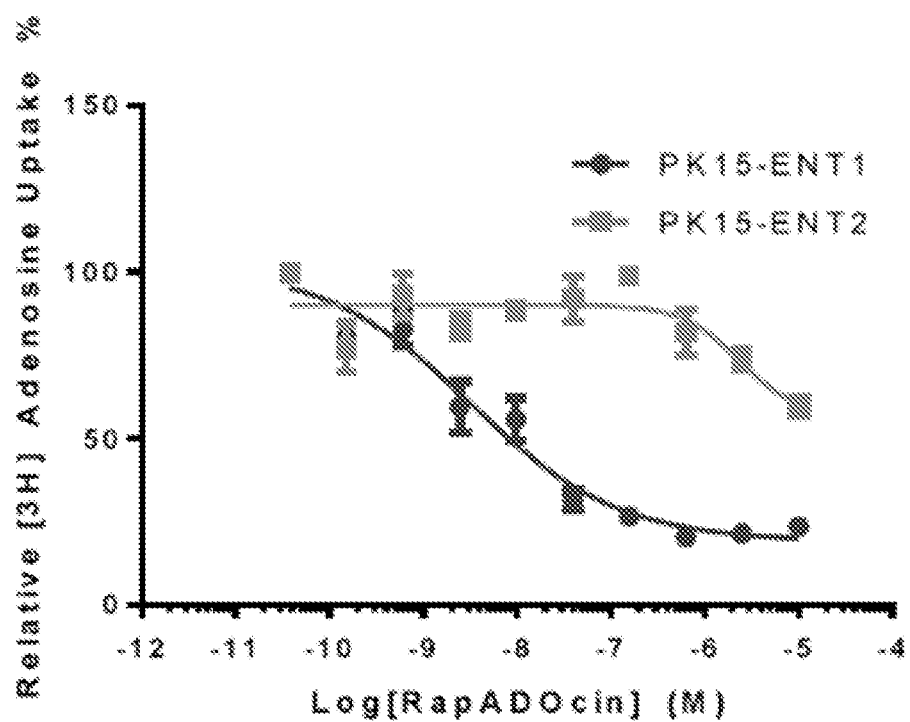
FIG. 1. Rapadocin inhibits $^3$H-Adenosine uptake by specifically inhibiting hENT1.

Other aspects and advantages of the invention will be apparent from the following description. Rapadocin Formula I (stylized as Rapadocin or also named JW95) is a synthetic macrocyclic small molecule. Rapadocin specifically inhibits the human equilibrative nucleoside transporter 1 (hENT1 or SLC29a1) with high potency.

Formula I

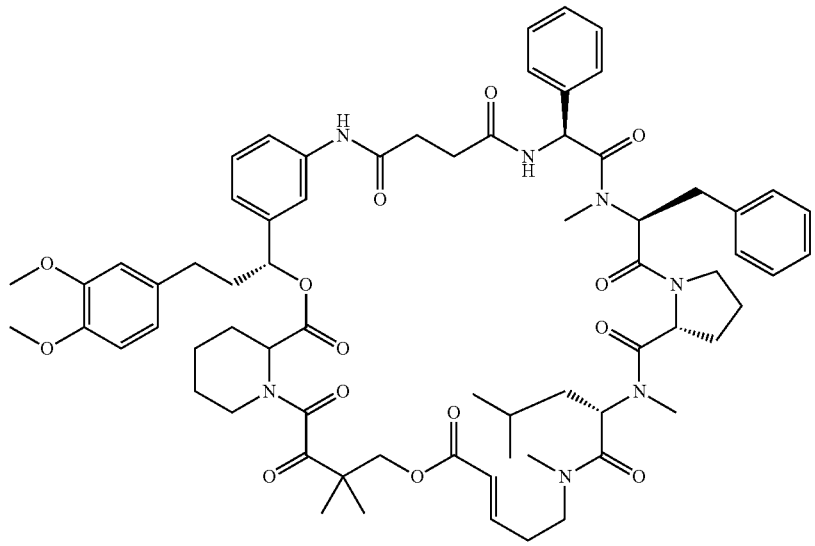

Rapadocin has been shown to be safely tolerated in animals via a kidney ischemia model. Rapadocin is a synthetic macrocycle composed of two 'domains'—a FKBD (FKBP12 binding domain) and a peptide domain. The FKBD can tolerate modifications at the dimethoxy phenyl region, notably to a dihydroxy phenyl analog. The peptidic fragment can tolerate a range of modifications with varying effects on ENT1 inhibition. Notably, the peptidic fragment can tolerate a few important modifications on the N-methyl phenylalanine residue.

The compound of Formula I is soluble up to 10 μM in aqueous solutions and has been shown to resist degradation over 5 days in cell culture media (37° C., 10% Fetal Bovine Serum).

Two different families of nucleoside transporters (NTs) have been characterized: equilibrative nucleoside transporters and concentrative nucleoside transporters. "Equilibrative nucleoside transporters" or "ENTs" refer to transporters that translocate substrate down the substrate's concentration gradient via passive transport or facilitated diffusion. ENT activity does not require a sodium ion (or other ion) gradient and are therefore termed "Na+-independent" transporters. ENTs are categorized into one of two subtypes based on sensitivity to inhibition by nitrobenzylmercaptopurine riboside (NBMBR).

Four members of the ENT family have been cloned and are termed ENT1, ENT2, ENT3, and ENT4. All 4 transport adenosine but differ from each other with respect to their ability to transport other nucleosides or nucleobases. ENT1 is an es subtype transporter. Exemplary polynucleotide sequences encoding human ENT1 include GenBank Accession No. U81375 and GenBank Accession No. AAC51103.1 represents the corresponding amino acid sequence. ENT1 is ubiquitously expressed in human and rodent tissues, although expression levels vary between tissues. ENT1 is known to transport a wide range of purine and pyrimidine nucleosides.

ENT2 is an ei subtype transporter. Exemplary polynucleotide sequences encoding human ENT2 include GenBank Accession No. AF029358 and GenBank Accession No. AAC39526 represents the corresponding amino acid sequence. ENT2 is expressed in a wide range of human and rodent tissues, including vascular endothelium, heart, brain, placenta, thymus, pancreas, prostate, kidney, and muscle, skeletal muscle, cardiac muscle, blood, skin, and ENT2-expressing cancer cells. ENT2-expressing cancer cells include, for example, certain renal tumor cells, breast tumor cells, prostate cancer cells, colon cancer cells, stomach cancer cells, leukemia cells, lung cancer cells, and ovarian cancer cells. Other types of ENT-2 expressing cancer cells are known in the art; (see e.g., Lu X et al., Journal of Experimental Therapeutics and Oncology 2:200-212, 2002, and Pennycooke M et al., Biochemical and Biophysical Research Communications 208, 951-959, 2001). ENT2 exhibits high expression levels in skeletal muscle. ENT2 is also expressed in the membrane of organelles such as the nucleus. ENT2 is known to transport a wide range of purine and pyrimidine nucleosides and nucleobases.

It is expected that inhibition of hENT1 by Rapadocin and its analogs will increase the extracellular concentrations of adenosine, thereby enhancing its signaling via adenosine receptors. Adenosine receptor agonists have been sought as treatments for multiple diseases. It is expected that Rapadocin will have similar activity as adenosine receptor agonists.

As used herein, a "therapeutically effective amount" of a compound, is the quantity of a compound which, when administered to an individual or animal, results in a sufficiently high level of that compound in the individual or animal to cause a discernible inhibition of the ENT1 transporters. The exact dosage and frequency of administration depends on the particular compound of the invention used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines. The invention compounds may be used for the manufacture of a medicine for treatment of a condition or a disease mediated by equilibrative nucleoside transporter END activity, in particular equilibrative nucleoside transporter ENT1 inhibitory activity.

Equilibrative nucleoside transporter ENT1 mediated conditions or disorders may include but are not limited to acute and chronic pain conditions including inflammatory pain, neuropathic pain, cancer pain, cardioprotection, cerebroprotection, traumatic brain injury (TBI), myeloprotection, neuroprotection, chronic pressure skin ulcers, wound healing, ischemia, anticonvulsant, organ transplant (organ preservation, like cardioplegia), sleep disorders, pancreatitis, glomerulonephritis, and antithrombotic (anti-platelet).

"Nucleoside transport pathways" refer to systems of one or more transport proteins that effect the transport of a substrate across one or more biological membranes. For example, a nucleoside transport pathway may mediate the step-wise transport of a substrate across the plasma membrane followed by the transport of the substrate across the membrane of an intracellular organelle. The transport proteins or nucleoside transporters responsible for such a step-wise translocation of a substrate across two biological membranes may be the same type of nucleoside transporter or may be of different types. In certain embodiments, the nucleoside transporter may be an equilibrative nucleoside transporter. In other embodiments, the nucleoside transporter may be a concentrative nucleoside transporter.

A "transport protein" or "transporter" is a protein that has a direct or indirect role in transporting a molecule across a membrane. The term includes, for example, membrane-bound proteins that recognize a substrate and effects its entry into, or exit from a cell by a carrier-mediated transporter or by receptor-mediated transport. Transporters may be present on plasma membranes or the membranes of intracellular organelles. Thus, transporters facilitate the transport of molecules into the cytoplasm or into an intracellular organelle.

The term "nucleoside" refers to a purine or pyrimidine base that is covalently linked to a 5-carbon sugar (i.e., pentose). When the sugar is ribose, the nucleoside is a ribonucleoside; when it is 2-deoxyribose, the nucleoside is a deoxyribonucleoside. Exemplary nucleosides include cytidine, uridine, adenosine, guanosine, and thymidine, and the corresponding deoxyribonucleosides, which form the basis of the nucleotides that form DNA and RNA.

The term "nucleoside analog" as used herein refers to a nucleoside in which the base moiety, the sugar moiety or both has been modified. Such analogs are generally synthetic and mimic natural nucleosides so that they may take the place of a nucleoside in cellular functions. For example, nucleosides may be incorporated into DNA or RNA in place of the natural corresponding nucleoside. Certain nucleoside analogs so incorporated can, for example, prevent further elongation of the nucleic acid chain during synthesis. Many nucleoside analogs have anti-viral or anti-cancer properties. Examples of nucleoside analogs include inosine, deoxyadenosine analogs such as didanosine (2',3'-dideoxyinosine, ddI) and vidarabine (9-O-D-ribofuranosyladenine), deoxycytidine analogs such as cytarabine (cytosine arabinoside, emtricitabine, lamivudine (2',3'-dideoxy-3'-thiacytidine, 3TC), and zalcitabine (2'-3'-dideoxycytidine, ddC), deoxyguanosine analogs such as abacavir, (deoxy-)thymidine analogs such as stavudine (2'-3'-didehydro-2'-3'-dideoxythymidine, d4T) and zidovudine (azidothymidine, or AZT), and deoxyuridine analogs such as idoxuridine and trifluridine.

The term "pharmaceutically acceptable salts" refers to physiologically and pharmaceutically acceptable salts of the compounds of the invention, e.g., salts that retain the desired biological activity of the parent compound and do not impart undesired toxicological effects thereto.

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

Example 1

Rapadocin Inhibits Nucleoside Uptake

Figure 2:
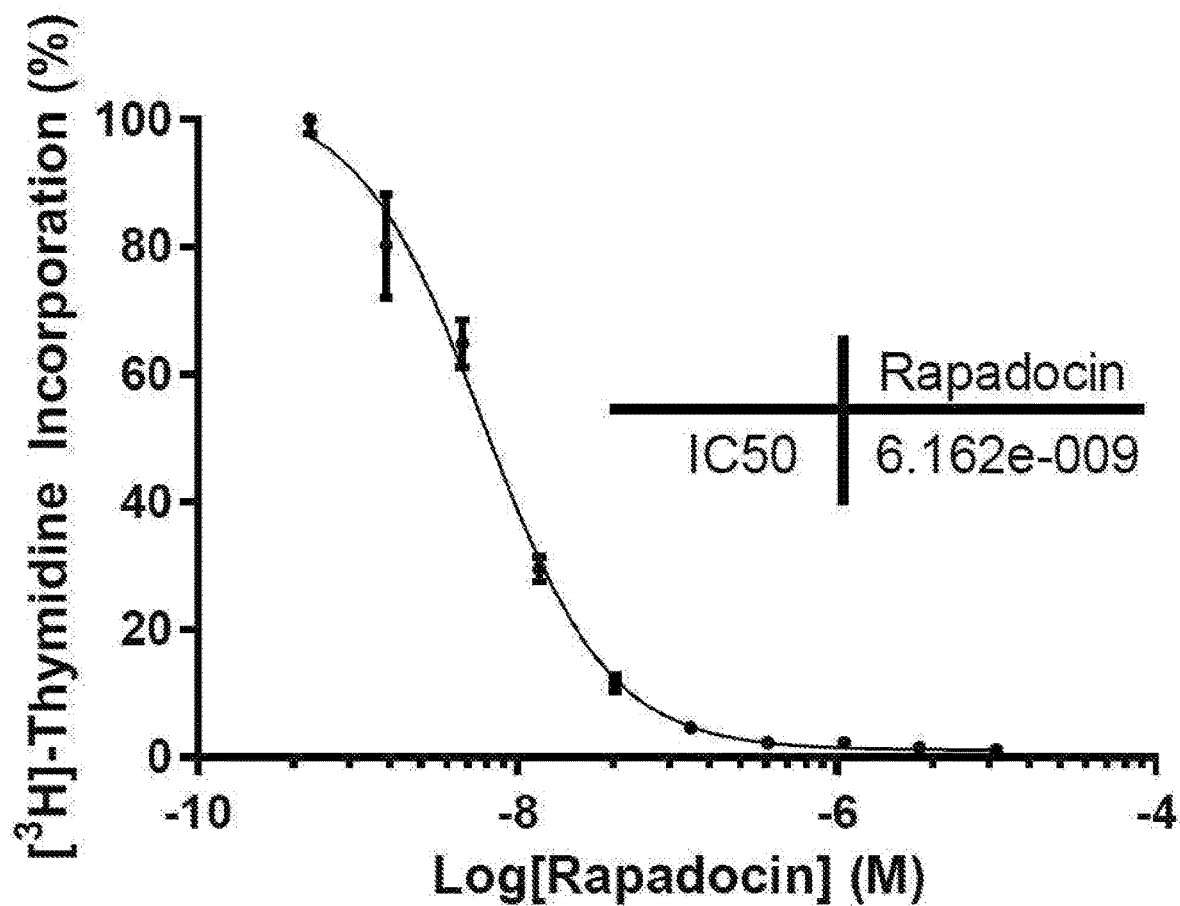
FIG. 2. Rapadocin inhibits $^3$H-Thymidine uptake in Human Umbilical Vein Endothelial Cells (HUVEC).
Figure 3:
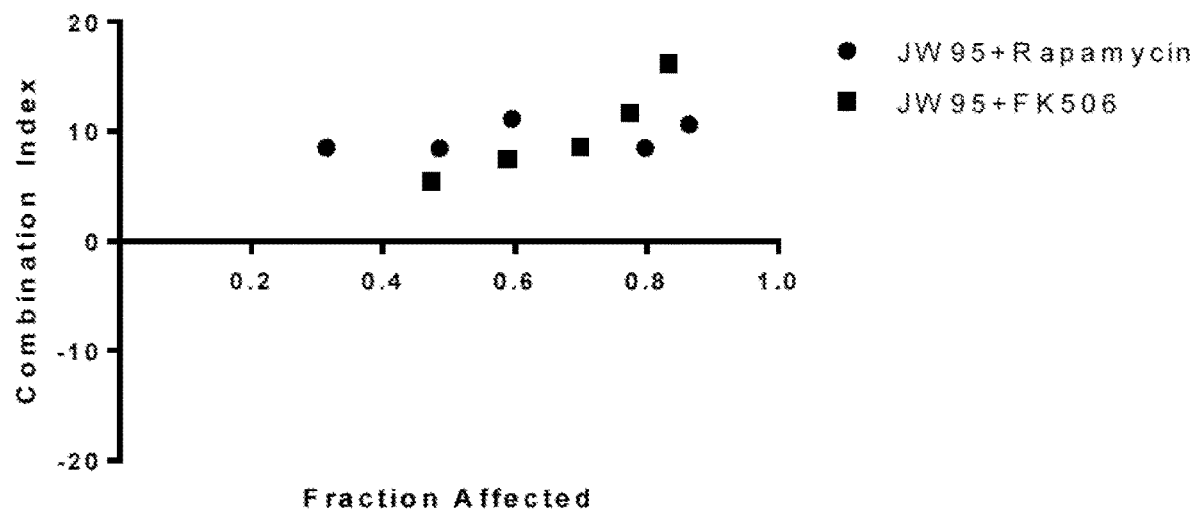
FIG. 3. Rapadocin's uptake inhibition is antagonized by FKBP12-binders Rapamycin and FK506.

Rapadocin potently and specifically inhibits nucleoside uptake by human equilibrative nucleoside uptake transporter 1 (hENT1) over hENT2, the two most predominant eqilibrative nucleoside transporters (FIG. 1). Rapadocin inhibits nucleoside uptake in at least seven cell lines and is predicted to inhibit nucleoside uptake in all human cell lines (see e.g., FIG. 2 and Table 1).

TABLE 1

$^3$H-Thymidine uptake in various cell lines

|  | HUVEC | 293T | RKO | A549 | HeLa | MCF-7 | MDA MB-231 |
|---|---|---|---|---|---|---|---|
| EC50 | 6.4 nM | 5.0 nM | 11.4 nM | 6.3 nM | 16.3 nM | 9.0 nM | 41.1 nM |

Rapafucin Analogs

TABLE 2

| Analog | Peptide | | | | $EC_{50}$ $^3$H-Tymidine uptake |
|---|---|---|---|---|---|
|  | Residue 1 | Residue 2 | Residue 3 | Residue 4 |  |
| JW95-1 | mGly | dPro | mGly | Phe | >1 uM |
| JW95-2 | mAla | dPro | mGly | Phe | >1 uM |
| JW95-3 | mLeu | dPro | mGly | Phe | >1 uM |
| JW95-4 | mSer | dPro | mGly | Phe | 1228 |

TABLE 2-continued

| Analog | Residue 1 | Residue 2 | Residue 3 | Residue 4 | EC$_{50}$ $^3$H-Tymidine uptake |
|---|---|---|---|---|---|
| JW95-5 | mPhe | dPro | mGly | Phe | 440 |
| JW95-6 | mGly | dPro | mAla | Phe | >1 uM |
| JW95-7 | mAla | dPro | mAla | Phe | >1 uM |
| JW95-8 | mLeu | dPro | mAla | Phe | >1 uM |
| JW95-9 | mSer | dPro | mAla | Phe | >1 uM |
| JW95-10 | mPhe | dPro | mAla | Phe | >1 uM |
| JW95-11 | mGly | dPro | mLeu | Phe | >1 uM |
| JW95-12 | mAla | dPro | mLeu | Phe | >1 uM |
| JW95-13 | mLeu | dPro | mLeu | Phe | 787 |
| JW95-14 | mSer | dPro | mLeu | Phe | 725 |
| JW95-15 | mPhe | dPro | mLeu | Phe | 377 |
| JW95-16 | mGly | dPro | mSer | Phe | >1 uM |
| JW95-17 | mAla | dPro | mSer | Phe | >1 uM |
| JW95-18 | mLeu | dPro | mSer | Phe | >1 uM |
| JW95-19 | mSer | dPro | mSer | Phe | >1 uM |
| JW95-20 | mPhe | dPro | mSer | Phe | >1 uM |
| JW95-21 | mGly | dPro | mPhe | Phe | >1 uM |
| JW95-22 | mAla | dPro | mPhe | Phe | 731 |
| JW95-23 | mLeu | dPro | mPhe | Phe | >1 uM |
| JW95-24 | mSer | dPro | mPhe | Phe | >1 uM |
| JW95-25 | mPhe | dPro | mPhe | Phe | >1 uM |
| 95-15-1 | mLeu | dPro | mPhe | Phe | 112 |
| 95-15-2 | mdLeu | dPro | mPhe | Phe | >1 uM |
| 95-15-3 | mLeu | dPro | mPhe | dhoPhe | >1 uM |
| 95-15-4 | Leu | dPro | mPhe | Phe | >1 uM |
| 95-15-5 | mIle | dPro | mPhe | Phe | >1 uM |
| 95-15-6 | mNle | dPro | mPhe | Phe | >1 uM |
| 95-15-7 | mLeu | Pro | mPhe | Phe | >1 uM |
| 95-15-8 | mLeu | Gly | mPhe | Phe | >1 uM |
| 95-15-9 | mLeu | dPro | mdPhe | Phe | >1 uM |
| 95-15-10 | mLeu | dPro | Phe | Phe | 182 |
| 95-15-11 | mLeu | dPro | mPhe | dPhe | >1 uM |
| 95-15-12 | mLeu | dPro | mPhe | hoPhe | >1 uM |
| 95-15-13 | mLeu | dPro | mPhe | Phg | 15 |
| 95-15-14 | mLeu | dPro | mPhe | PheF | >1 uM |
| 95-15-15 | mLeu | dPro | mPhe | PheCl | >1 uM |
| 95-15-16 | mLeu | dPro | mPhe | PheI | >1 uM |
| 95-15-17 | mLeu | dPro | mPhe | Tyr | >1 uM |
| 95-15-18 | mLeu | dPro | mPhe | TyrBu | >1 uM |
| 95-15-19 | mLeu | dPro | mPhe | PheNO2 | >1 uM |
| 95-15-20 | mLeu | dPro | mPhe | mPhe | >1 uM |
| 95-15-21 | mLeu | dPro | mPhe | Cha | 112 |
| 95-15-22 | mLeu | dPro | mPhe | NaI | >1 uM |
| 95-15-23 | mLeu | dPro | mPhe | biPhe | >1 uM |
| Rapadocin | mLeu | dPro | mPhe | Phg | 6.16 |
| 95-15-13-2 | mLeu | dHoPro | mPhe | Phg | 1920 |
| 95-15-13-3 | mLeu | dPro | Phe | Phg | 64 |
| 95-15-13-4 | mLeu | dPro | Pyr | Phg | 266 |
| 95-15-13-5 | mLeu | dPro | hoPhe | Phg | 15 |
| 95-15-13-6 | mLeu | dPro | Phg | Phg | 261 |
| 95-15-13-7 | mLeu | dPro | PheF | Phg | 56.7 |
| 95-15-13-8 | mLeu | dPro | PheCl | Phg | 123 |
| 95-15-13-9 | mLeu | dPro | PheI | Phg | 62.5 |
| 95-15-13-10 | mLeu | dPro | Tyr | Phg | 9.64 |
| 95-15-13-11 | mLeu | dPro | TyrOMe | Phg | 32.6 |
| 95-15-13-12 | mLeu | dPro | PheNO2 | Phg | 130 |
| 95-15-13-13 | mLeu | dPro | Cha | Phg | 199 |
| 95-15-13-14 | mLeu | dPro | NaI | Phg | 87.8 |
| 95-15-13-15 | mLeu | dPro | biPhe | Phg | 194 |
| JW95Diol[1] Formula II | mLeu | dPro | mPhe | Phg | 3 |
| JW95TyrBiotin Formula III | mLeu | dPro | Tyr(PEG)2Biotin | Phg | 64 |
| JW95S2Biotin | mLeu | dPro | mPhe | Phg | >1 uM |
| JW95TyrDiaz Formula IV | mLeu | dPro | Tyr---Diaz | Phg | 20 nM |

[1]JW95Diol utilizes a modified FKBD where the two methoxy groups are replaced with hydroxyl groups Table 2 discloses the potency of various Rapadocin analogs.
Structures of selected Rapadocin analogs are represented as follows:
Formula II
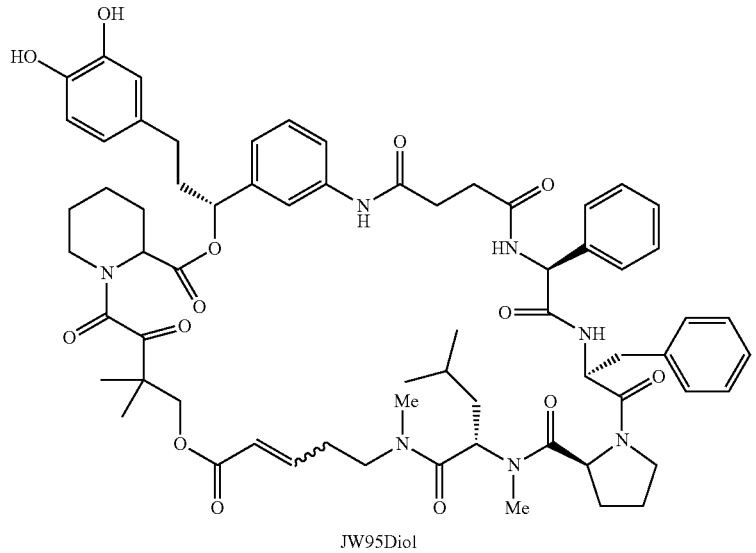
JW95Diol
Formula III
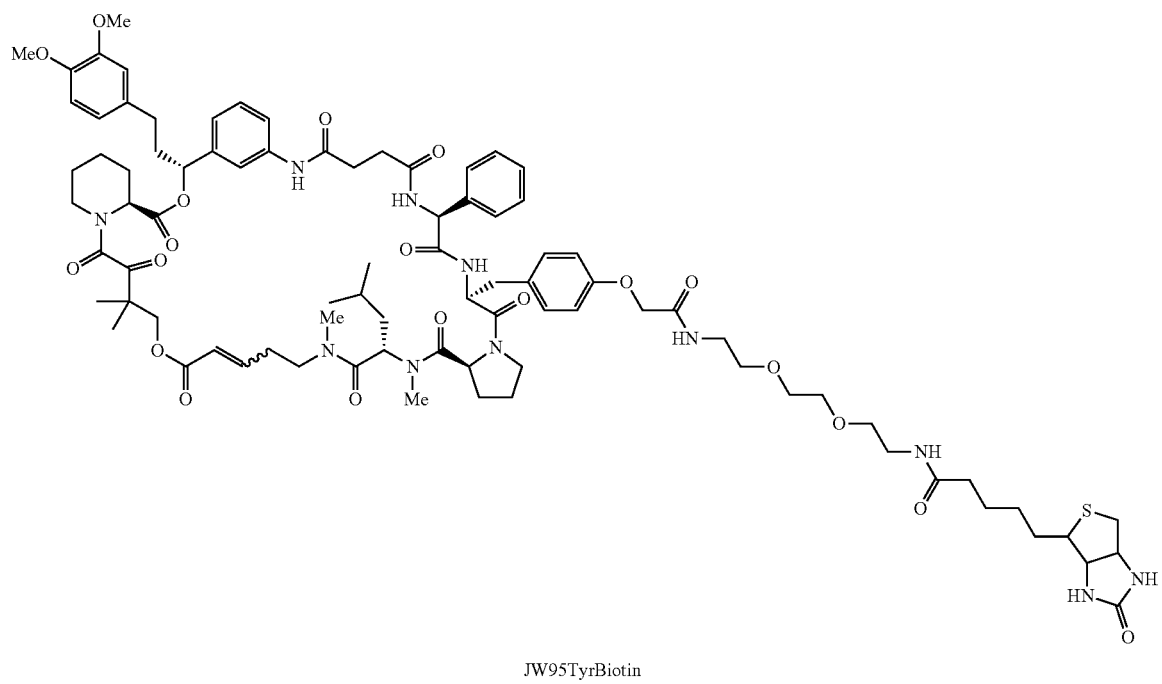
JW95TyrBiotin -continued
Formula IV
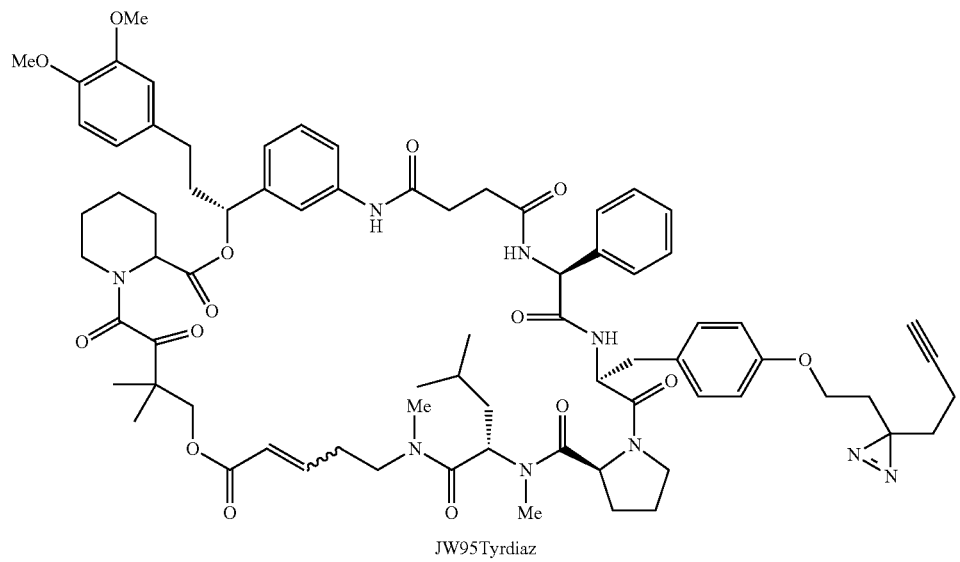
JW95Tyrdiaz
Formula V
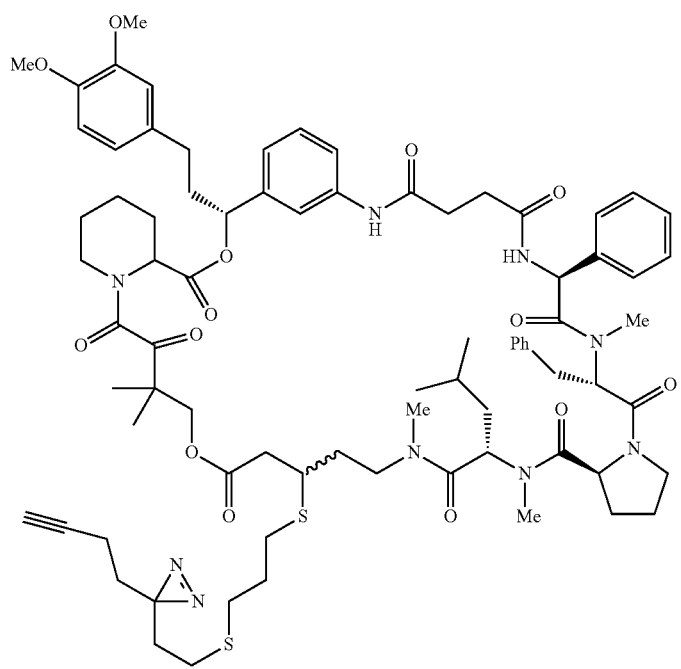
JW95-S2-diaz

Example 2

Human and Animal Models

Figure 4:
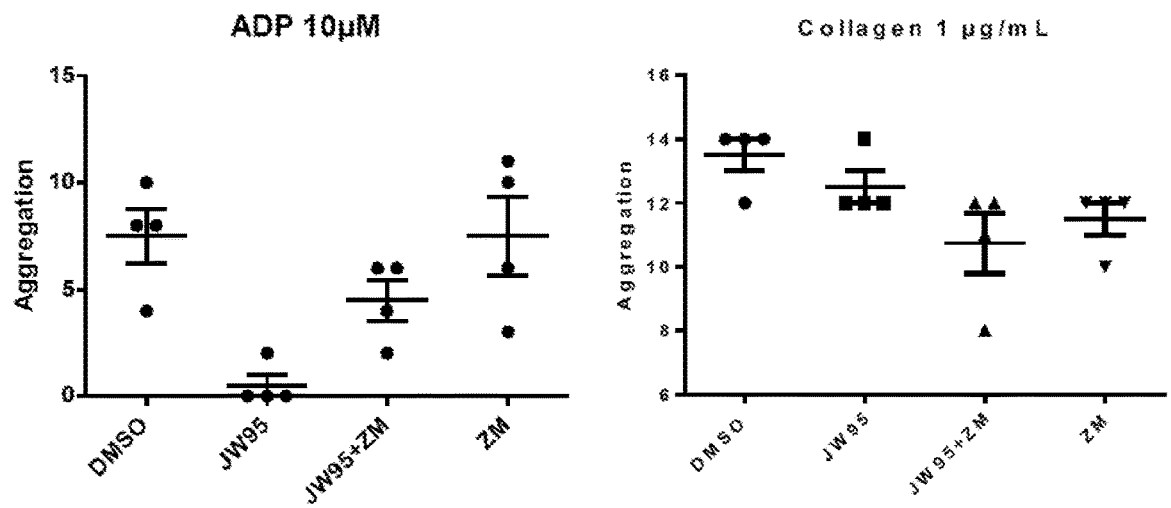
FIG. 4. Rapadocin inhibits platelet aggregation in human blood when activated by ADP.
Figure 5:
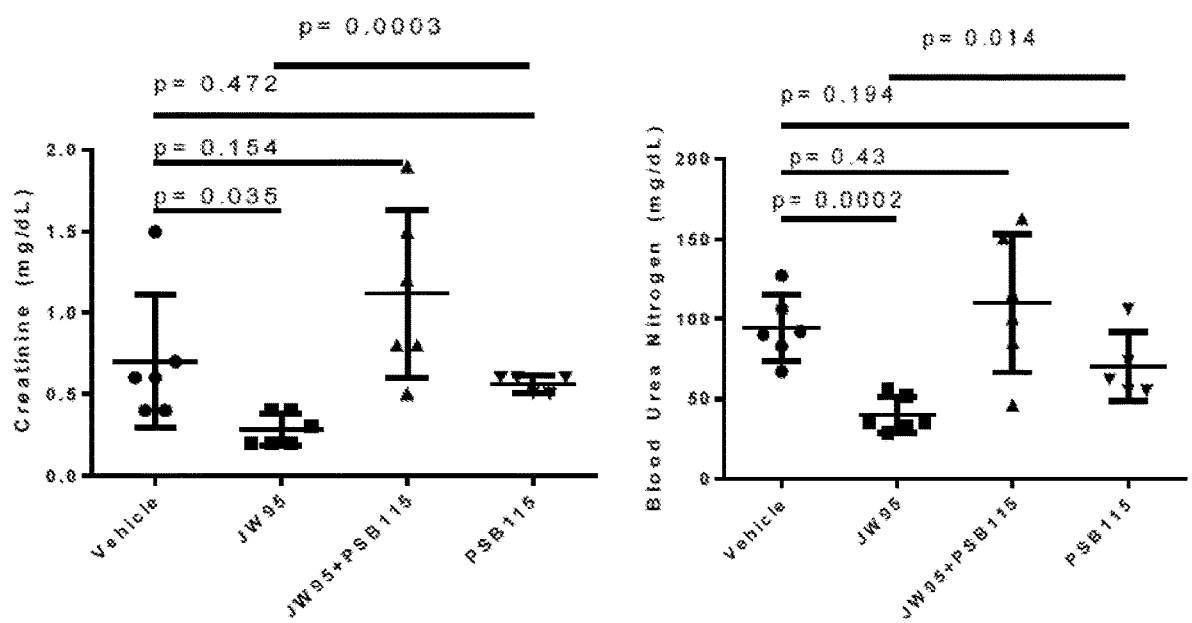
FIG. 5. Rapadocin protects against kidney ischemia reperfusion injury in a mouse model.

Two human and animal models have been studied to show the efficacy of Rapadocin (FIGS. 4 and 5). Under several physiological conditions, adenosine is released into the blood where it can act on adenosine receptors. Normally, this adenosine (ADO) is rapidly reabsorbed via ENT1. In the presence of Rapadocin, uptake is inhibited and ADO is able to produce enhanced signaling leading to several potentially beneficial physiological responses.

Example 3

Additional compounds that can be used to improve Pharmacokinetics/Pharmacodynamics and solubility of the leads include the following:

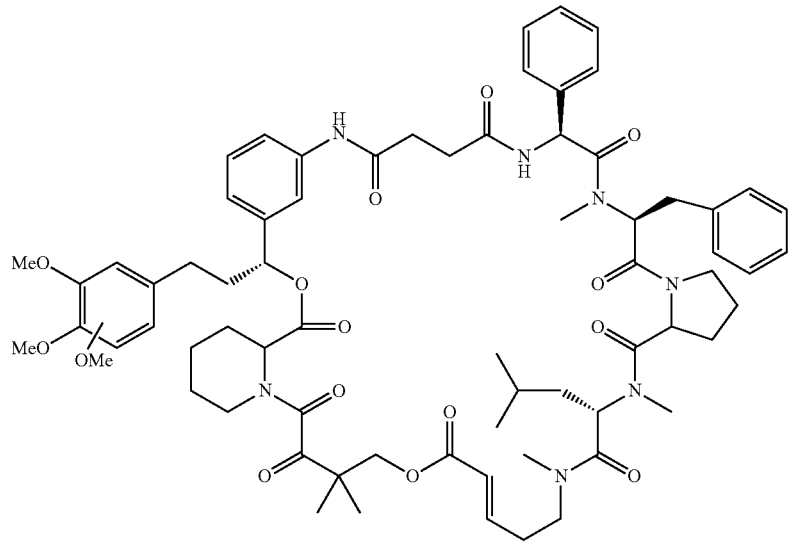

Formula VI

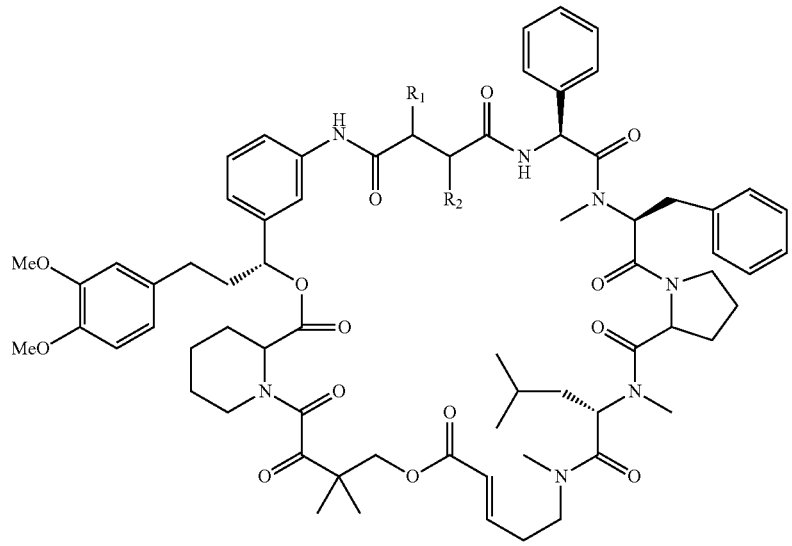

Formula VII ($R_1$ = OH, $NH_2$, SH, H;
$R_2$ = OH, $NH_2$, SH, H)

Formula VIII
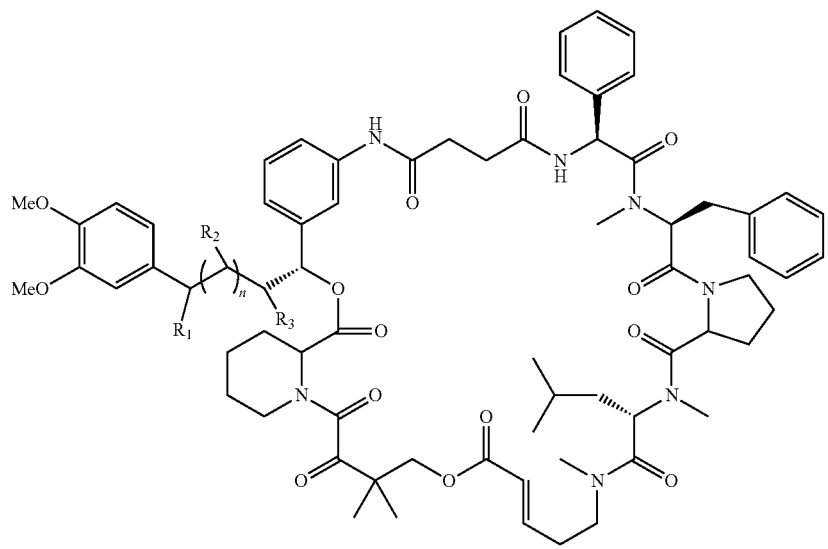
n = 0-6
R₁-R₃; individually or in
combination, = methyl, ethyl, propyl,
isopropyl, phenyl, OH, NH₂, SH.
Formula IX
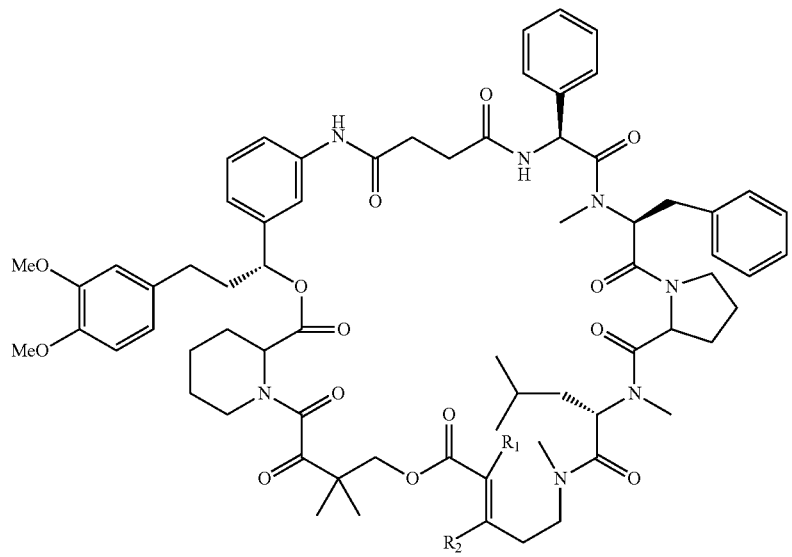
($R_1$ = OH, NH₂, SH, H;
$R_2$ = OH, NH₂, SH, H)

Formula X
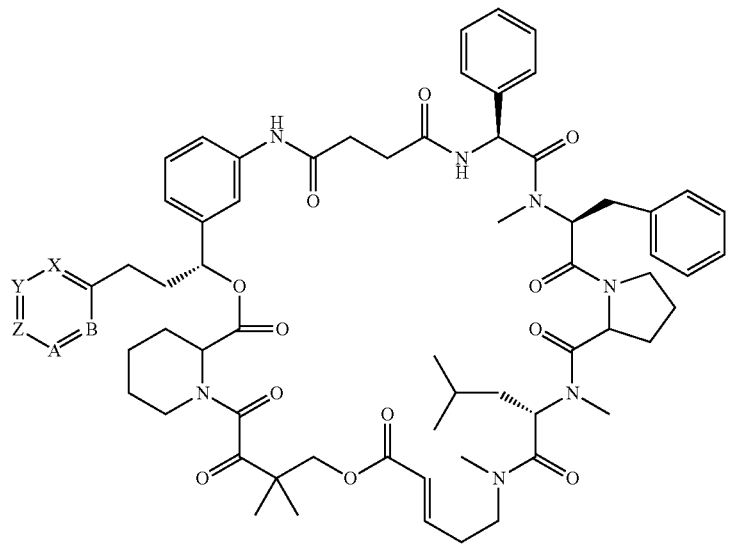
A = B = X = Y = Z = C;
A, B, X, Y, Z = N, P;
A = B = N, X = Y = Z = H;
X = Z = N, Y = A = B = H;
X = A = N, Y = Z = B = H;
X = Y = Z = N, A = B = H;
X = Y = Z = A = N, B = H;
Formula XI
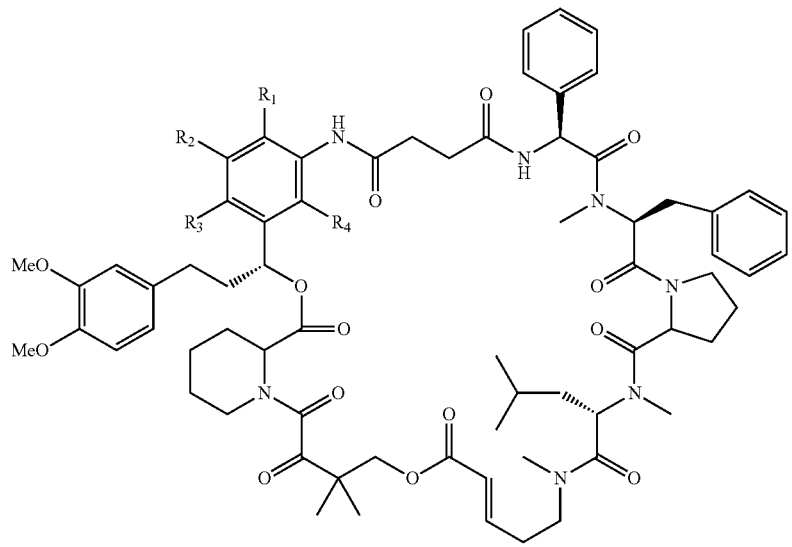
$R_1$-$R_4$: individually or in combination, = methyl, ethyl, propyl, isopropyl, phenyl, OH, $NH_2$, SH.

Formula XII
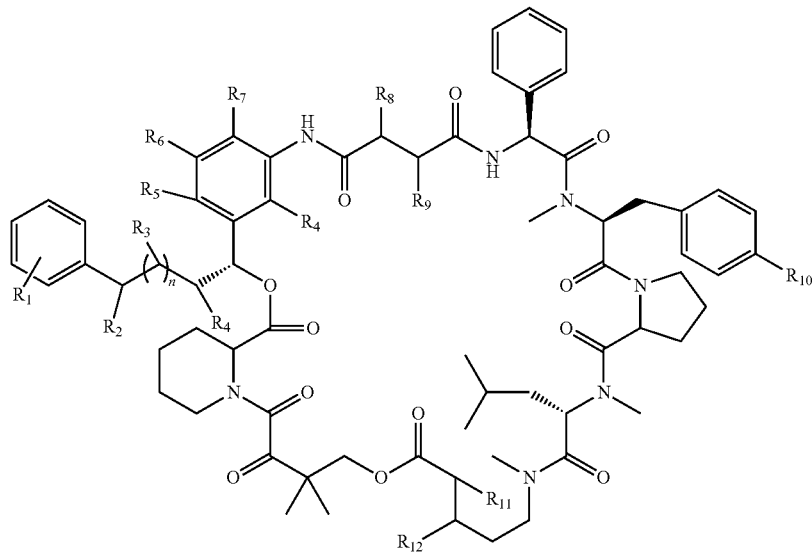
(X, Y = O, NH, S;
L = alkyl, polyether or
modified linkers with
varing chain length.)
R₁-R₁₂: individually = 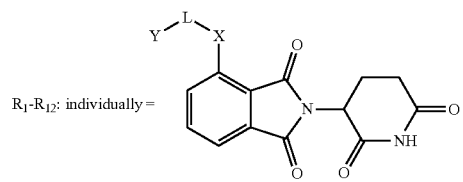

Example 4
Scheme 1
Synthetic route for Rapadocin with FKBD 8
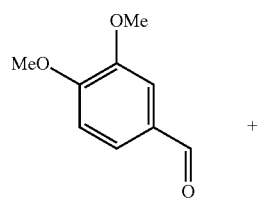
+
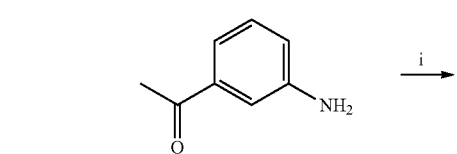 →i→
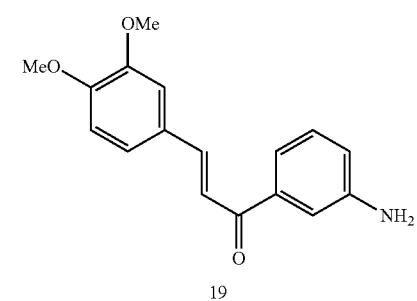 →ii 29% over 2 steps→
19
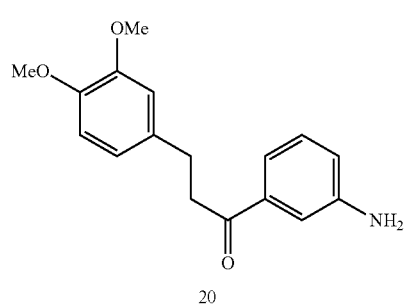 →vii→
20
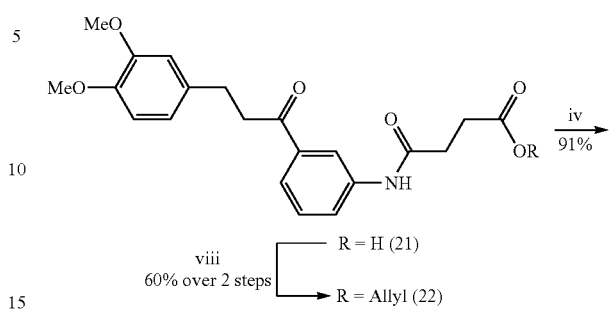 →iv 91%→
viii 60% over 2 steps ⎡ R = H (21)
⎣ R = Allyl (22)
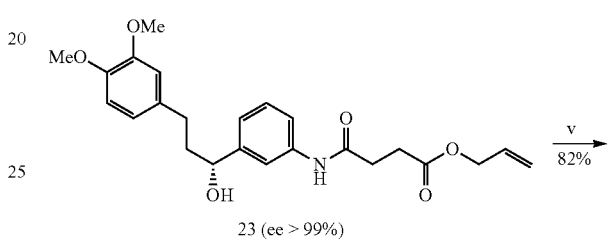
23 (ee > 99%) →v 82%→
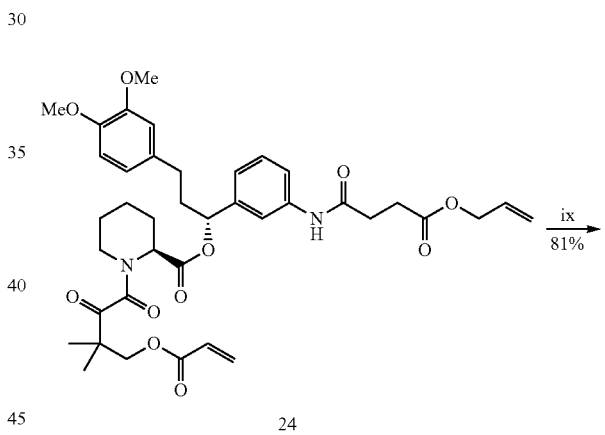
24 →ix 81%→
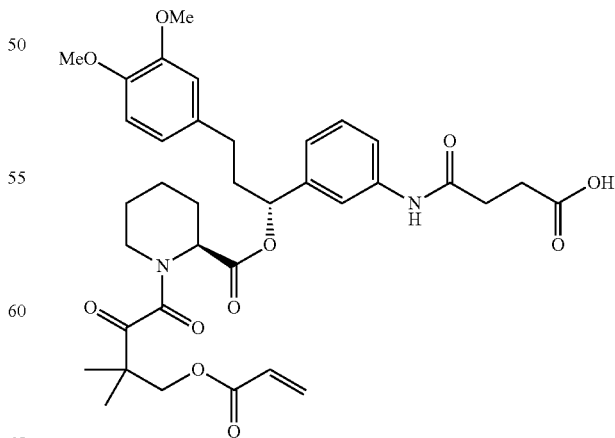
11

-continued

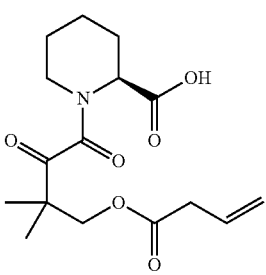

8

Reaction conditions: i) KOH, H₂O/EtOH (1/20), RT, 6 h; ii) Pd/C (10%), H₂, MeOH, RT, 1.5 h; iii) tert-butyl 2-bromoacetate, K₂CO₃, DMF/acetone (1/2), RT, 4 h; iv) (+)- DIPCl, THF, -20° C to RT, 5 h; v) FKBD 8, benzoyl chloride, DMAP (5%), NEt₃, CH₂Cl₂, RT, 4 h; vi) TFA (10%), CH₂Cl₂, RT, 6 h; vii) succinic anhydride, DMAP (5%), CH₂Cl₂, RT, 3 h; viii) allyl bromide, Cs₂CO₃, DMF, RT, 2 h; ix) Pd(PPh₃)₄ (10%), N-methylaniline, THF, RT, 6 h.

Example 5

Compounds that can be used to improve Pharmacokinetics/Pharmacodynamics and solubility are represented by the following generic structure:

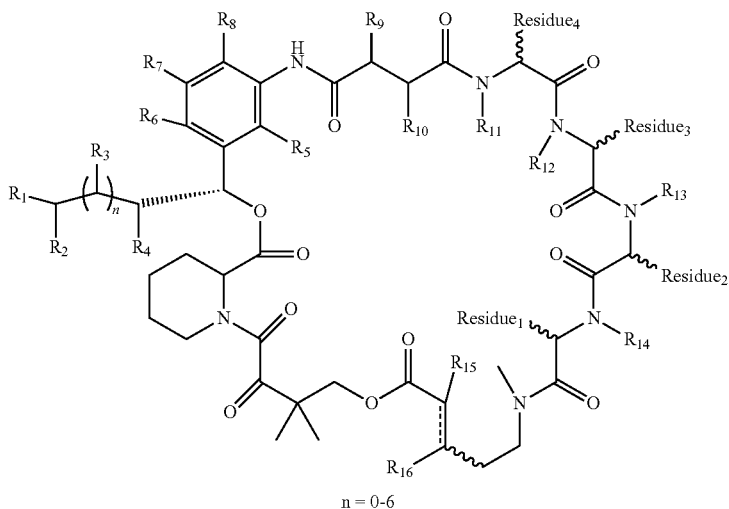

n = 0-6

$R_1$;

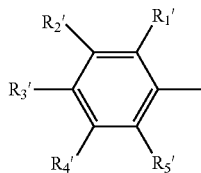

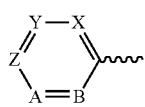

Wherein A, B, X, Y, Z=C, N, or P either individually or in combination.

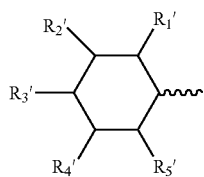

Wherein $R_1'$-$R_5'$=OH, NH₂, SH, CN, H, OAc, or OMe individually or in combination.

Wherein $R_3'$-$R_5'$=OH, $NH_2$, SH, H, OAc, OMe individually or in combination.

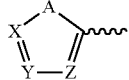

Wherein A, X, Y, or Z=CHn' (n'=0-2), O, N. S, wherever appropriate individually or in combination.

$R_2$-$R_4$: H, methyl, ethyl, propyl, isopropyl, phenyl, OH, $NH_2$, SH, CN, individually or in combination.

$R_5$-$R_8$: methyl, propyl, isopropyl, phenyl, OH, $NH_2$, SH, CN, individually or in combination.

$R_9$=OH, $NH_2$, SH, CN, H;

$R_{10}$=OH, $NH_2$, SH, CN, H, $R_{13-14}$=H or Me $R_{15}$=OH, $NH_2$, SH, CN, H:

$R_{16}$=OH, $NH_2$, SH, CN, H.

The bond between the carbons bearing $R_{15}$ and $R_{16}$ can be either a single or a double bond in either E or Z configuration.

Residues 1-4 can be any amino acid building block listed in Table 3 or its modified version.

TABLE 3

Amino Acid Building Blocks for Residues in the Effector Domain

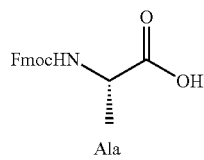

Ala

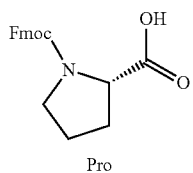

Pro

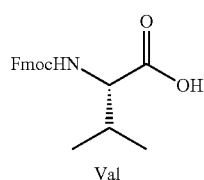

Val

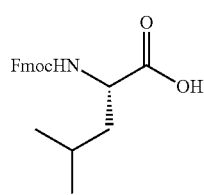

Leu

TABLE 3-continued

Amino Acid Building Blocks for Residues in the Effector Domain

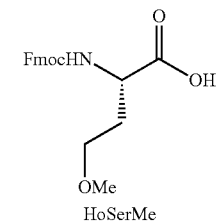

HoSerMe

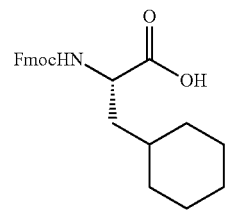

ChA

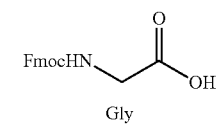

Gly

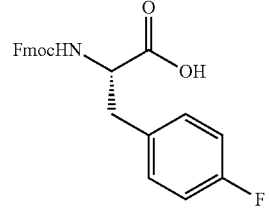

PhF

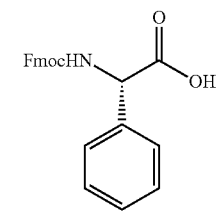

PhG

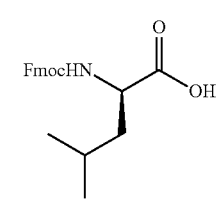

dLeu

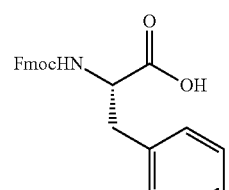

Phe

TABLE 3-continued
Amino Acid Building Blocks for Residues in the Effector Domain
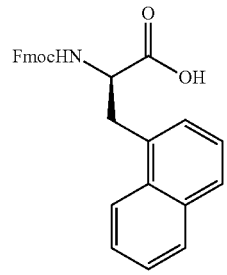
Nal
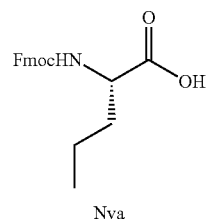
Nva
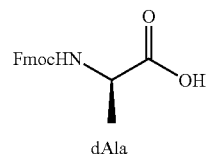
dAla
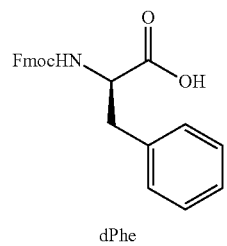
dPhe
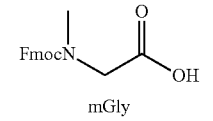
mGly
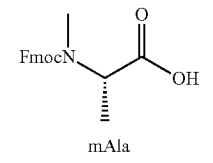
mAla
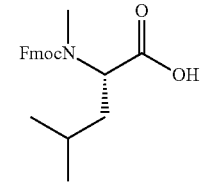
mLeu
TABLE 3-continued
Amino Acid Building Blocks for Residues in the Effector Domain
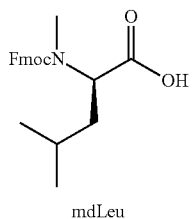
mdLeu
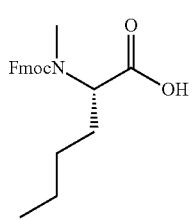
mNle
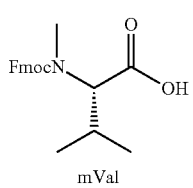
mVal
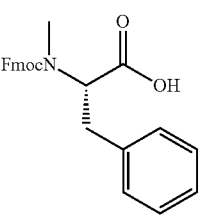
mPhe
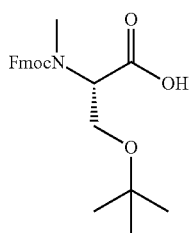
mSerBu
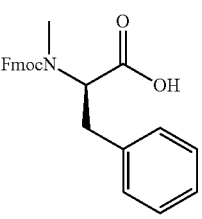
mdPhe TABLE 3-continued Amino Acid Building Blocks for Residues in the Effector Domain

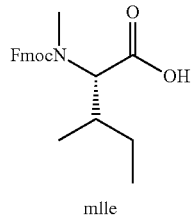

mIle

References 11-15 describe the use of adenosine agonists in the treatment of various diseases. Based upon the information disclosed in these references, one of ordinary skill in the art would recognize that the compounds disclosed in this application could be used to treat these diseases. See e.g., Table 2 of Reference 15 as it relates to the treatment of arrhythmias.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

The following references are each relied upon and incorporated herein in their entirety.
1. Passer, B. J. et al. Identification of the ENT1 Antagonists Dipyridamole and Dilazep as Amplifiers of Oncolytic Herpes Simplex Virus-1 Replication. Cancer Res. 70, 3890-3895 (2010).
2. Kose, M. & Schiedel, A. C. Nucleoside/nucleobase transporters: drug targets of the future? Future Med. Chem. 1, 303-326 (2009).
3. Melendez, R. I. & Kalivas, P. W. Last call for adenosine transporters. Nat. Neurosci. 7, 795-796 (2004).
4. Choi, D.-S. et al. The type 1 equilibrative nucleoside transporter regulates ethanol intoxication and preference. Nat. Neurosci. 7, 855-861 (2004).
5. Puetz, C. et al. *Nitrobenzylthioinosine compounds for relief of pain*. (Google Patents, 2008). at <https://www.google.com/patents/US7358235>
6. Sawynok, J. in *Adenosine* 343-360 (Springer, 2013). at <http://link.springer.com/chapter/10.1007/978-1-4614-3903-5_17>
7. Bauerle, J. D., Grenz, A., Kim, J.-H., Lee, H. T. & Eltzschig, H. K. Adenosine Generation and Signaling during Acute Kidney Injury. J. Am. Soc. Nephrol. 22, 14-20 (2011).
8. Grenz, A. et al. The Reno-Vascular A2B Adenosine Receptor Protects the Kidney from Ischemia. PLoS Med. 5, e137 (2008).
9. Grenz, A. et al. Equilibrative nucleoside transporter 1 (ENT1) regulates postischemic blood flow during acute kidney injury in mice. J. Clin. Invest. 122, 693-710 (2012).
10. Zimmerman, M. A. et al. Equilibrative nucleoside transporter (ENT)-1-dependent elevation of extracellular adenosine protects the liver during ischemia and reperfusion. Hepatology 58, 1766-1778 (2013).
11. Mohamadnejad, M. et al. Adenosine inhibits chemotaxis and induces hepatocyte-specific genes in bone marrow mesenchymal stem cells. Hepatology 51(3), 963-73 (2010).
12. Wen, J. et al. Adenosine signaling: good or bad in erectile function? Arterioscler Thromn Vasc Biol 32(4), 845-50 (2012).
13. Xu, Z. et al. ENT1 inhibition attenuates epileptic seizure severity via regulation of glutamatergic neurotransmission. Neuromolecular Med. 17(1), 1-11 (2015).
14. Chen, J. et al. Adenosine receptors as drug targets-what are the challenges? Nat Rev Drug Disc 12(4), 265-86 (2013).
15. Sachdeva, S. et al. Adenosine and its receptors as therapeutic targets: An overview. Saudi Pharmaceutical Journal 21, 245-253 (2013).
16. Griffith et al., Biochim. Bioph. Acta 1286:153-181 (1986).
17. Lu X et al., Journal of Experimental Therapeutics and Oncology 2:200-212, 2002.
18. Pennycooke M et al., Biochemical and Biophysical Research Communications 208, 951-959, 2001.

What is claimed is:

1. A compound selected from the group consisting of:

Formula I

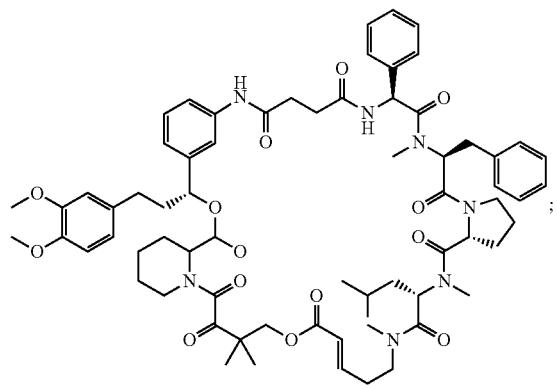

Formula II

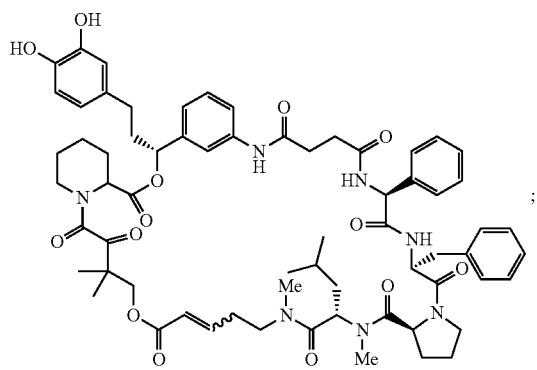

Formula III
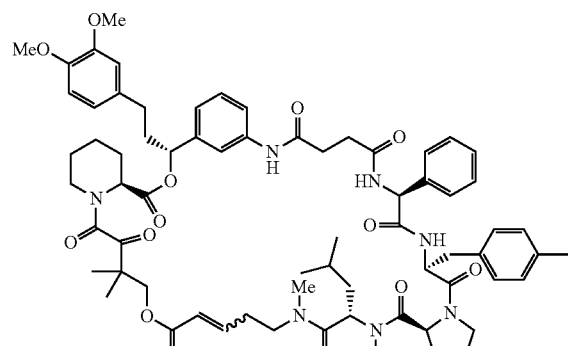
Formula IV
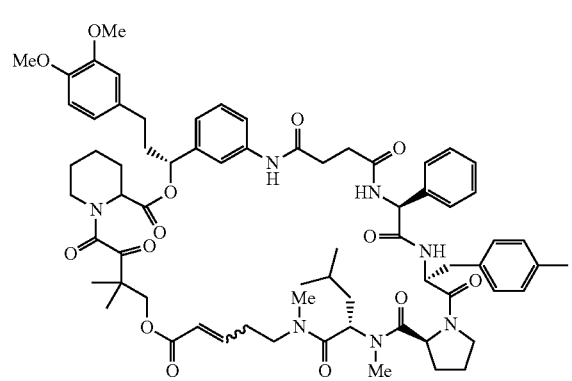
Formula V
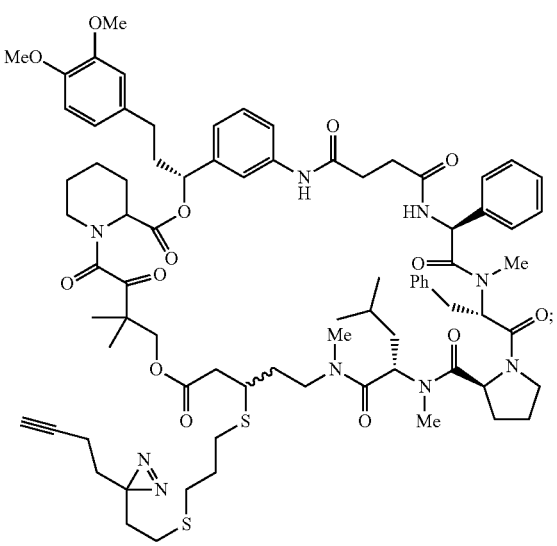
Formula VI
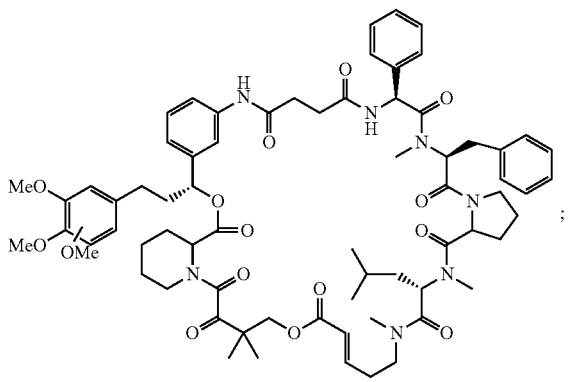
Formula VII
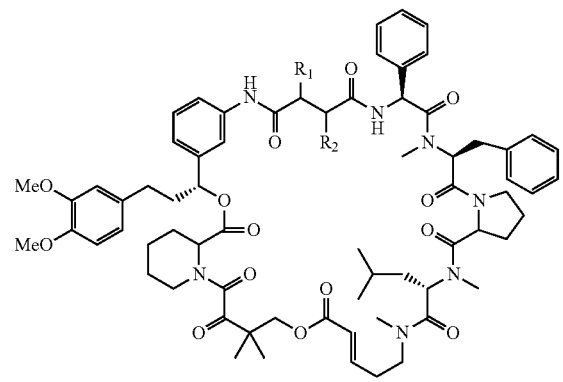
wherein each $R_1$ and $R_2$ is independently selected from the group consisting of OH, $NH_2$, SH, and hydrogen;

Formula VIII

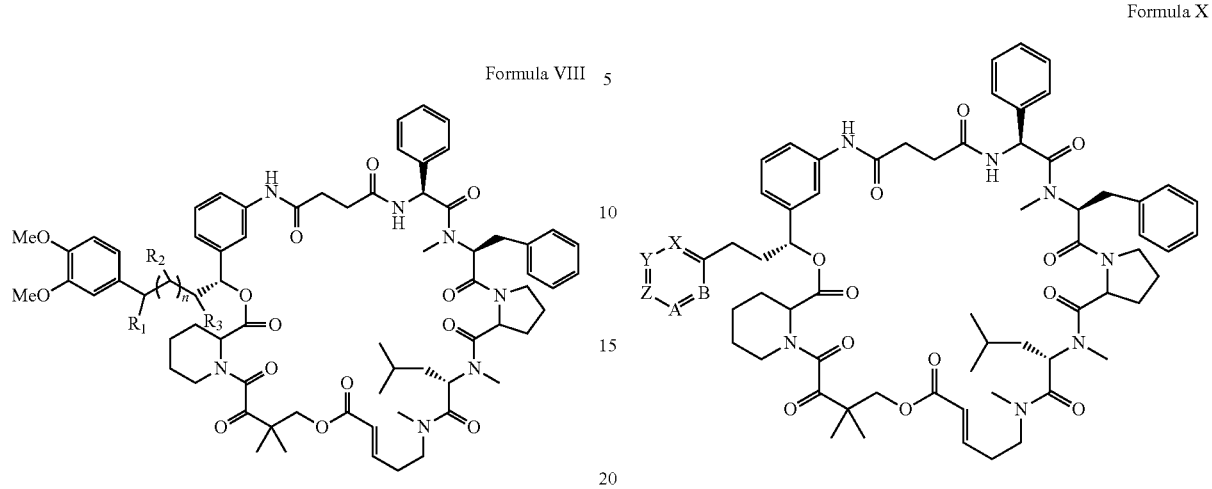

Formula X wherein n is an integer selected from 0 to 6, each $R_1$, $R_2$, and $R_3$ is independently selected from the group consisting of methyl, ethyl, propyl, isopropyl, phenyl, OH, $NH_2$, and SH;

wherein each A, B, X, Y, and Z is independently selected from the group consisting of CH and N;

Formula IX

Formula XI

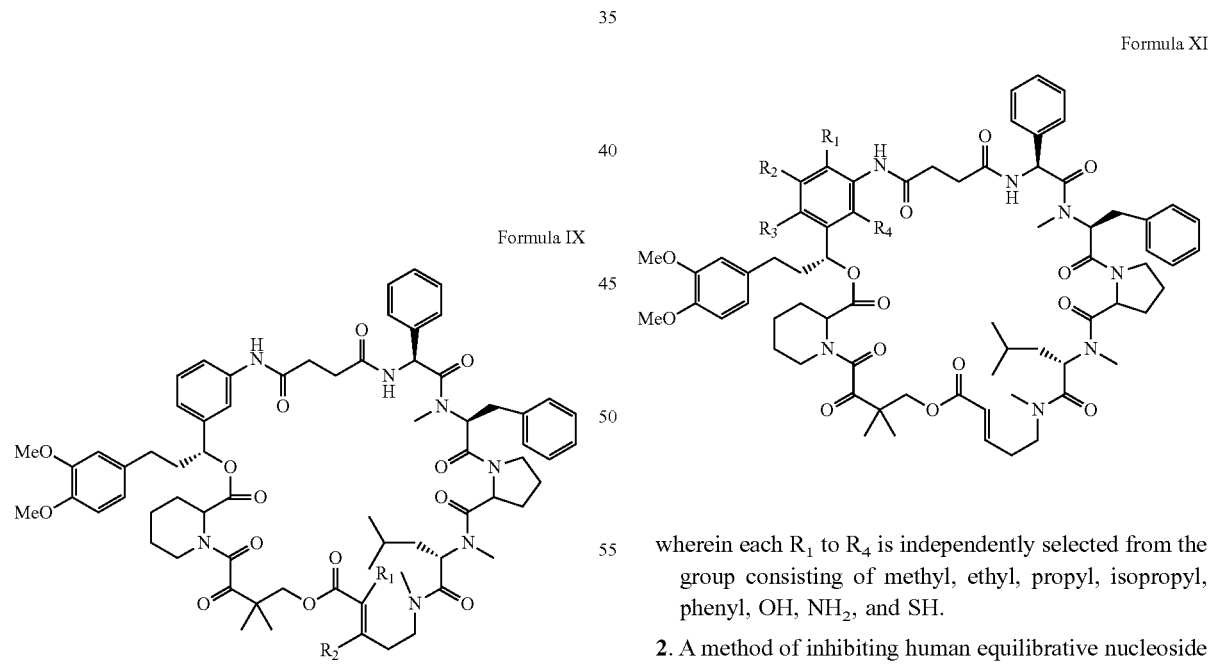

wherein each $R_1$ to $R_4$ is independently selected from the group consisting of methyl, ethyl, propyl, isopropyl, phenyl, OH, $NH_2$, and SH.

2. A method of inhibiting human equilibrative nucleoside transporter 1 (ENT1) comprising administering to a subject in need thereof an effective amount of a compound of claim 1, thereby inhibiting ENT1.

3. A method of increasing adenosine signaling comprising administering to a subject in need thereof an effective amount of a compound of claim 1, thereby increasing adenosine signaling.

wherein each $R_1$ and $R_2$ is independently selected from the group consisting of OH, $NH_2$, SH, and hydrogen;

4. A macrocyclic compound according to Formula (I):

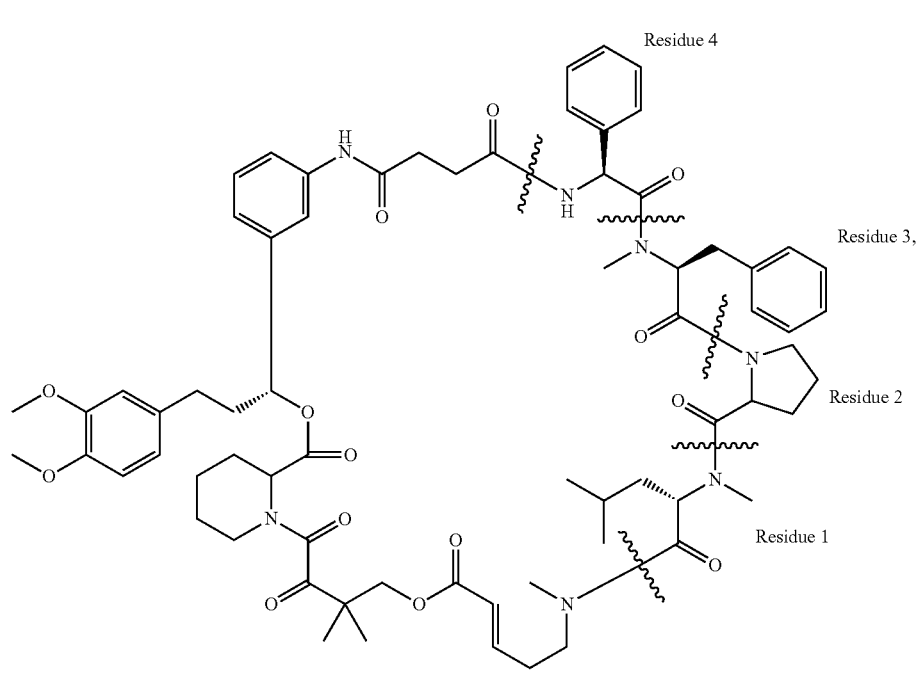

Formula (I)

wherein residue 1, residue 2, residue 3, and residue 4 are exchanged and selected from below:

| | Peptide | | | |
|---|---|---|---|---|
| | Residue 1 | Residue 2 | Residue 3 | Residue 4 |
| JW95-1 | mGly | dPro | mGly | Phe |
| JW95-2 | mAla | dPro | mGly | Phe |
| JW95-3 | mLeu | dPro | mGly | Phe |
| JW95-4 | mSer | dPro | mGly | Phe |
| JW95-5 | mPhe | dPro | mGly | Phe |
| JW95-6 | mGly | dPro | mAla | Phe |
| JW95-7 | mAla | dPro | mAla | Phe |
| JW95-8 | mLeu | dPro | mAla | Phe |
| JW95-9 | mSer | dPro | mAla | Phe |
| JW95-10 | mPhe | dPro | mAla | Phe |
| JW95-11 | mGly | dPro | mLeu | Phe |
| JW95-12 | mAla | dPro | mLeu | Phe |
| JW95-13 | mLeu | dPro | mLeu | Phe |
| JW95-14 | mSer | dPro | mLeu | Phe |
| JW95-15 | mPhe | dPro | mLeu | Phe |
| JW95-16 | mGly | dPro | mSer | Phe |
| JW95-17 | mAla | dPro | mSer | Phe |
| JW95-18 | mLeu | dPro | mSer | Phe |
| JW95-19 | mSer | dPro | mSer | Phe |
| JW95-20 | mPhe | dPro | mSer | Phe |
| JW95-21 | mGly | dPro | mPhe | Phe |
| JW95-22 | mAla | dPro | mPhe | Phe |
| JW95-23 | mLeu | dPro | mPhe | Phe |
| JW95-24 | mSer | dPro | mPhe | Phe |
| JW95-25 | mPhe | dPro | mPhe | Phe |
| 95-15-1 | mLeu | dPro | mPhe | Phe |
| 95-15-2 | mdLeu | dPro | mPhe | Phe |
| 95-15-3 | mLeu | dPro | mPhe | dhoPhe |
| 95-15-4 | Leu | dPro | mPhe | Phe |
| 95-15-5 | mIle | dPro | mPhe | Phe |
| 95-15-6 | mNle | dPro | mPhe | Phe |
| 95-15-7 | mLeu | Pro | mPhe | Phe |
| 95-15-8 | mLeu | Gly | mPhe | Phe |
| 95-15-9 | mLeu | dPro | mdPhe | Phe |
| 95-15-10 | mLeu | dPro | Phe | Phe |
| 95-15-11 | mLeu | dPro | mPhe | dPhe |
| 95-15-12 | mLeu | dPro | mPhe | hoPhe |
| 95-15-13 | mLeu | dPro | mPhe | Phg |
| 95-15-14 | mLeu | dPro | mPhe | PheF |
| 95-15-15 | mLeu | dPro | mPhe | PheCl |
| 95-15-16 | mLeu | dPro | mPhe | PheI |
| 95-15-17 | mLeu | dPro | mPhe | Tyr |
| 95-15-18 | mLeu | dPro | mPhe | TyrBu |
| 95-15-19 | mLeu | dPro | mPhe | PheNO2 |
| 95-15-20 | mLeu | dPro | mPhe | mPhe |
| 95-15-21 | mLeu | dPro | mPhe | Che |
| 95-15-22 | mLeu | dPro | mPhe | Nal |
| 95-15-23 | mLeu | dPro | mPhe | biPhe |
| 95-15-13-2 | mLeu | dHoPro | mPhe | Phg |
| 95-15-13-3 | mLeu | dPro | Phe | Phg |
| 95-15-13-4 | mLeu | dPro | Pyr | Phg |
| 95-15-13-5 | mLeu | dPro | hoPhe | Phg |
| 95-15-13-6 | mLeu | dPro | Phg | Phg |
| 95-15-13-7 | mLeu | dPro | PheF | Phg |
| 95-15-13-8 | mLeu | dPro | PheCl | Phg |
| 95-15-13-9 | mLeu | dPro | PheI | Phg |
| 95-15-13-10 | mLeu | dPro | Tyr | Phg |
| 95-15-13-11 | mLeu | dPro | TyrOMe | Phg |
| 95-15-13-12 | mLeu | dPro | PheNO2 | Phg |
| 95-15-13-13 | mLeu | dPro | Cha | Phg |
| 95-15-13-14 | mLeu | dPro | Nal | Phg |
| 95-15-13-15 | mLeu | dPro | biPhe | Phg |
| JW9552Biotin | mLeu | dPro | mPhe | Phg. |

* * * * *